United States Patent
Aubailly et al.

(10) Patent No.: US 10,835,352 B2
(45) Date of Patent: Nov. 17, 2020

(54) INTRAORAL SCANNER AND COMPUTING SYSTEM FOR CAPTURING IMAGES AND GENERATING THREE-DIMENSIONAL MODELS

(71) Applicant: 3D Imaging and Simulation Corp. Americas, Sterling, VA (US)

(72) Inventors: Mathieu Aubailly, Washington, DC (US); Sigrid Smitt, Great Falls, VA (US); Scott A. Mudge, Washington, DC (US); Qingyun Wang, Potomac, MD (US)

(73) Assignee: 3D Imaging and Simulation Corp. Americas, Sterling, VA (US)

( * ) Notice: Subject to any disclaimer, the term of this patent is extended or adjusted under 35 U.S.C. 154(b) by 244 days.

(21) Appl. No.: 15/925,093

(22) Filed: Mar. 19, 2018

(65) Prior Publication Data

US 2019/0282342 A1    Sep. 19, 2019

(51) Int. Cl.
*A61C 9/00* (2006.01)
*A61B 1/04* (2006.01)
*A61B 1/06* (2006.01)
*A61B 1/24* (2006.01)

(52) U.S. Cl.
CPC ............... *A61C 9/006* (2013.01); *A61B 1/04* (2013.01); *A61B 1/06* (2013.01); *A61B 1/24* (2013.01)

(58) Field of Classification Search
USPC ......................................... 396/16
See application file for complete search history.

(56) References Cited

U.S. PATENT DOCUMENTS

| | | | | |
|---|---|---|---|---|
| 5,003,166 A | * | 3/1991 | Girod | G01B 11/2513 250/201.4 |
| 5,702,249 A | * | 12/1997 | Cooper | H04N 5/2251 433/29 |
| 5,771,067 A | * | 6/1998 | Williams | A61B 1/00177 348/66 |
| 5,865,725 A | * | 2/1999 | Arai | A61B 1/00177 600/169 |
| 6,002,424 A | * | 12/1999 | Rapa | H04N 7/183 348/223.1 |

(Continued)

FOREIGN PATENT DOCUMENTS

| | | |
|---|---|---|
| AU | 2013101537 A4 | 12/2013 |
| CA | 2824665 A1 | 7/2012 |

(Continued)

*Primary Examiner* — Rodney E Fuller
(74) *Attorney, Agent, or Firm* — Dunlap Bennett & Ludwig, PLLC

(57) ABSTRACT

An intraoral scanner and computing system for capturing images and generating three-dimensional models. The intraoral scanner includes a handle, a mouthpiece extending from the handle, a flood illuminator projecting light from the mouthpiece, a structured light projector projecting a light pattern from the mouthpiece, and stereo camera capturing images through the mouthpiece. An optimal image of each of different materials within the captured images are combined to create a high dynamic range image. The structured light pattern in the high dynamic range image is used to determine three-dimensional measurements and create a three-dimensional model.

16 Claims, 9 Drawing Sheets

(56) References Cited

U.S. PATENT DOCUMENTS

| | | | |
|---|---|---|---|
| 6,181,369 B1* | 1/2001 | Ooshima | A61B 1/00177 348/66 |
| 6,276,934 B1* | 8/2001 | Rakocz | A61B 1/247 433/29 |
| D468,429 S | 1/2003 | Bareth et al. | |
| 6,606,113 B2* | 8/2003 | Nakamura | A61B 1/00193 348/45 |
| 6,937,348 B2* | 8/2005 | Geng | G01B 11/2509 356/602 |
| 7,354,402 B2* | 4/2008 | Hoarau | A61C 19/00 433/31 |
| 8,411,917 B2* | 4/2013 | Gandyra | G01B 11/03 382/128 |
| D741,935 S | 10/2015 | Sundheim et al. | |
| D742,518 S | 11/2015 | Barak et al. | |
| 9,757,020 B1* | 9/2017 | Elazar | H04N 5/23241 |
| 2001/0026315 A1* | 10/2001 | Ooshima | A61B 1/247 348/66 |
| 2004/0117052 A1* | 6/2004 | Geng | A61B 1/00142 700/117 |
| 2004/0166471 A1 | 8/2004 | Schussler et al. | |
| 2005/0090749 A1* | 4/2005 | Rubbert | A61B 1/00193 600/473 |
| 2007/0009150 A1* | 1/2007 | Suwa | G01B 11/2545 382/154 |
| 2007/0064242 A1* | 3/2007 | Childers | G01S 17/86 356/601 |
| 2009/0087050 A1* | 4/2009 | Gandyra | G01B 11/03 382/128 |
| 2010/0209002 A1* | 8/2010 | Thiel | A61B 5/0064 382/206 |
| 2012/0056993 A1* | 3/2012 | Luqman | A61B 1/00045 348/47 |
| 2012/0237889 A1* | 9/2012 | Nowak | G01B 11/2513 433/29 |
| 2013/0010080 A1* | 1/2013 | Ray | G01B 11/2527 348/47 |
| 2013/0108981 A1* | 5/2013 | Duret | A61B 5/1077 433/30 |
| 2013/0120533 A1* | 5/2013 | Milch | G06T 7/521 348/45 |
| 2013/0286174 A1* | 10/2013 | Urakabe | A61B 1/00009 348/66 |
| 2014/0146142 A1* | 5/2014 | Duret | H04N 13/243 348/47 |
| 2014/0255868 A1* | 9/2014 | Jesenko | A61C 9/0046 433/28 |
| 2014/0272764 A1* | 9/2014 | Miller | A61B 1/0684 433/27 |
| 2016/0191901 A1* | 6/2016 | Stegall | A61C 9/0053 348/49 |
| 2016/0220105 A1* | 8/2016 | Duret | A61B 6/022 |
| 2016/0262856 A1* | 9/2016 | Atiya | A61C 9/006 |
| 2017/0181815 A1* | 6/2017 | Pulido | A61C 9/0053 |
| 2017/0202483 A1* | 7/2017 | Sorimoto | A61B 1/00009 |
| 2017/0202650 A1* | 7/2017 | Bohm | A61C 13/0006 |
| 2017/0289523 A1* | 10/2017 | Lee | H04N 13/207 |
| 2018/0028292 A1* | 2/2018 | Pesach | A61C 9/0053 |
| 2018/0080828 A1* | 3/2018 | Fink | A61B 5/0088 |
| 2020/0060550 A1* | 2/2020 | Pesach | G06K 9/3233 |

FOREIGN PATENT DOCUMENTS

| | | |
|---|---|---|
| CN | 105640484 A | 6/2016 |
| DE | 10105497 A1 | 8/2002 |
| DE | 19619951 C2 | 2/2003 |
| DE | 102012102580 A1 | 9/2013 |
| EP | 2554107 A1 | 2/2013 |
| JP | 3414857 B2 | 6/2003 |
| JP | 2007143963 A | 6/2007 |
| JP | 2011056154 A | 3/2011 |
| JP | 2011110072 A | 6/2011 |
| JP | 2011110073 A | 6/2011 |
| JP | 2011172609 A | 9/2011 |
| JP | 2012020033 A | 2/2012 |
| JP | 2012075690 A | 4/2012 |
| JP | 2014516609 A | 7/2014 |
| MX | 2010003528 A | 9/2011 |
| WO | 2009139110 A1 | 11/2009 |
| WO | 2010057336 A1 | 5/2010 |
| WO | 2010094805 A1 | 8/2010 |
| WO | 2011050496 A1 | 5/2011 |
| WO | 2011052129 A1 | 5/2011 |
| WO | 2012060063 A1 | 5/2012 |
| WO | 2015016340 A1 | 2/2015 |
| WO | 2016032470 A1 | 3/2016 |
| WO | 2016113745 A1 | 7/2016 |

* cited by examiner

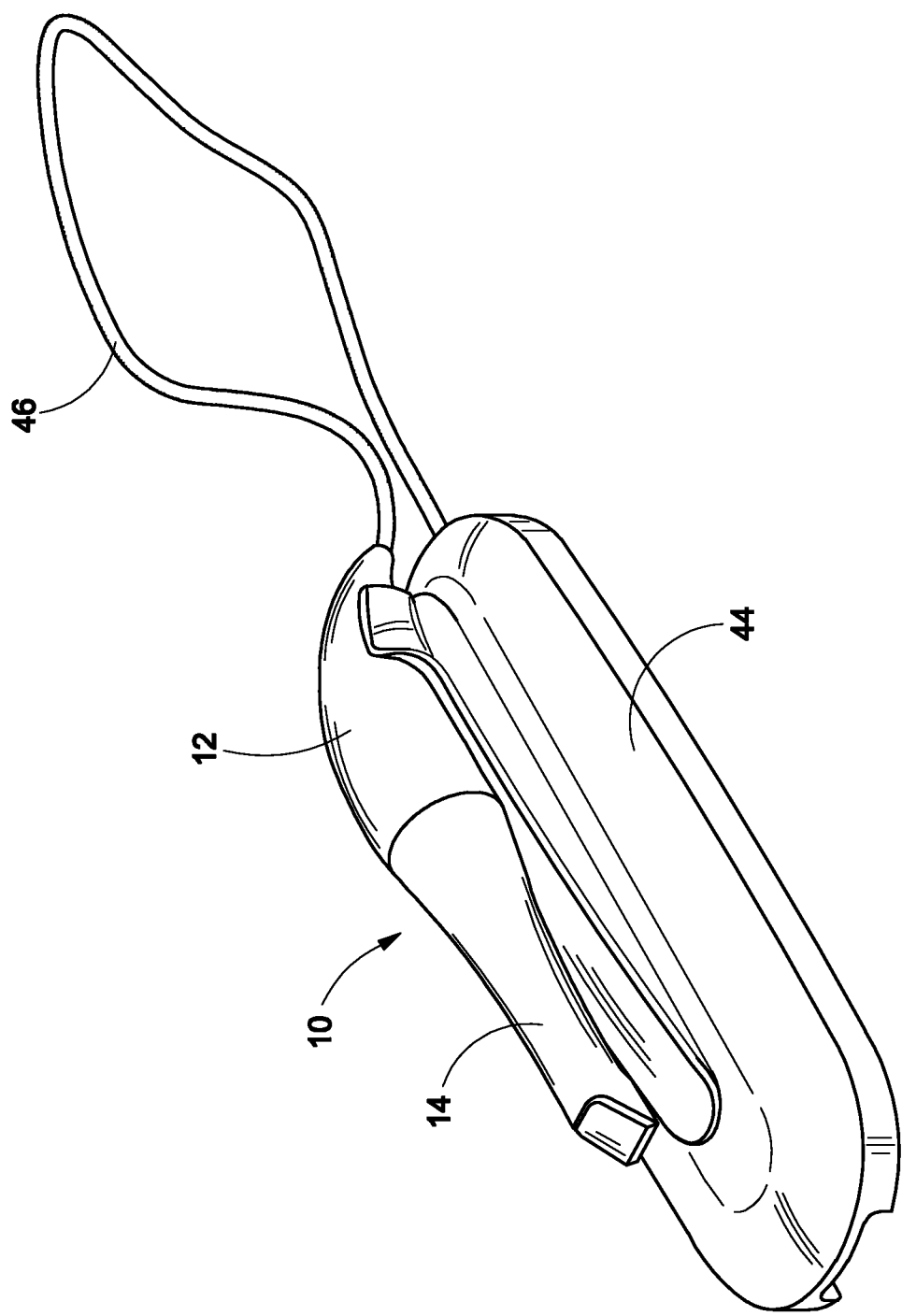

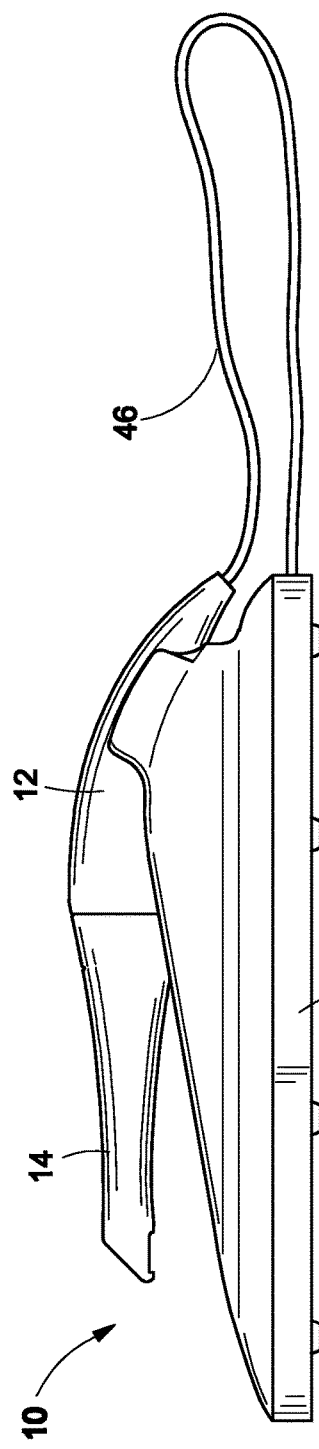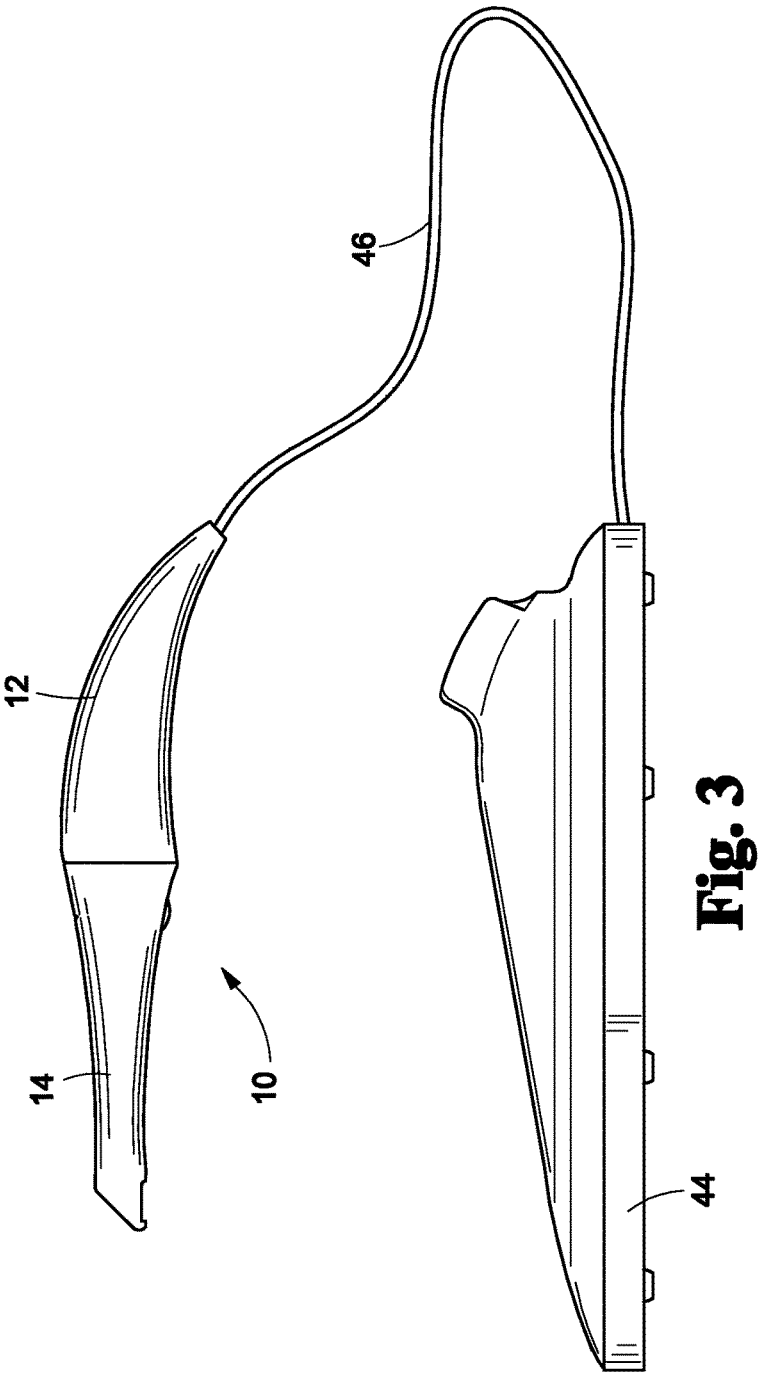

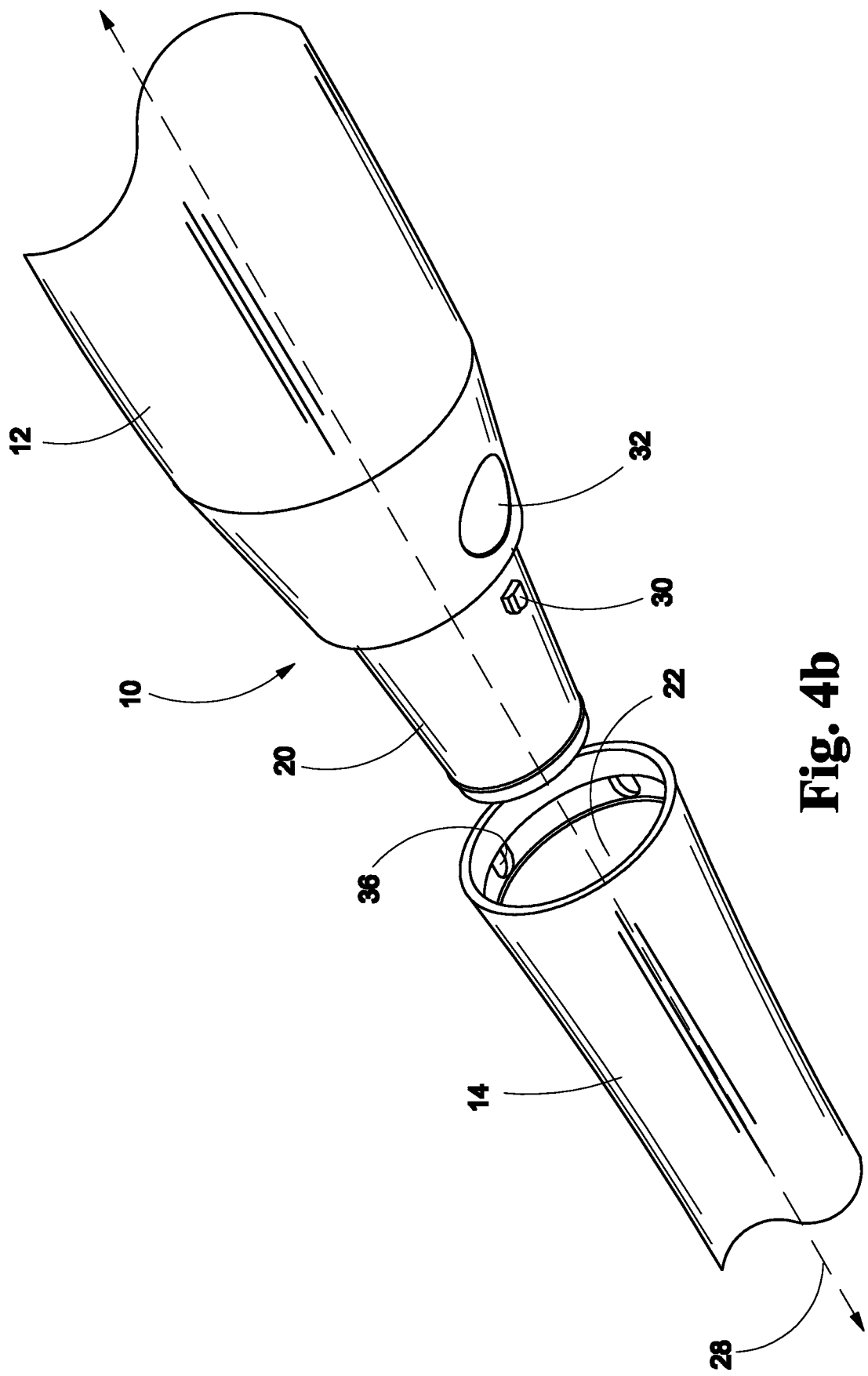

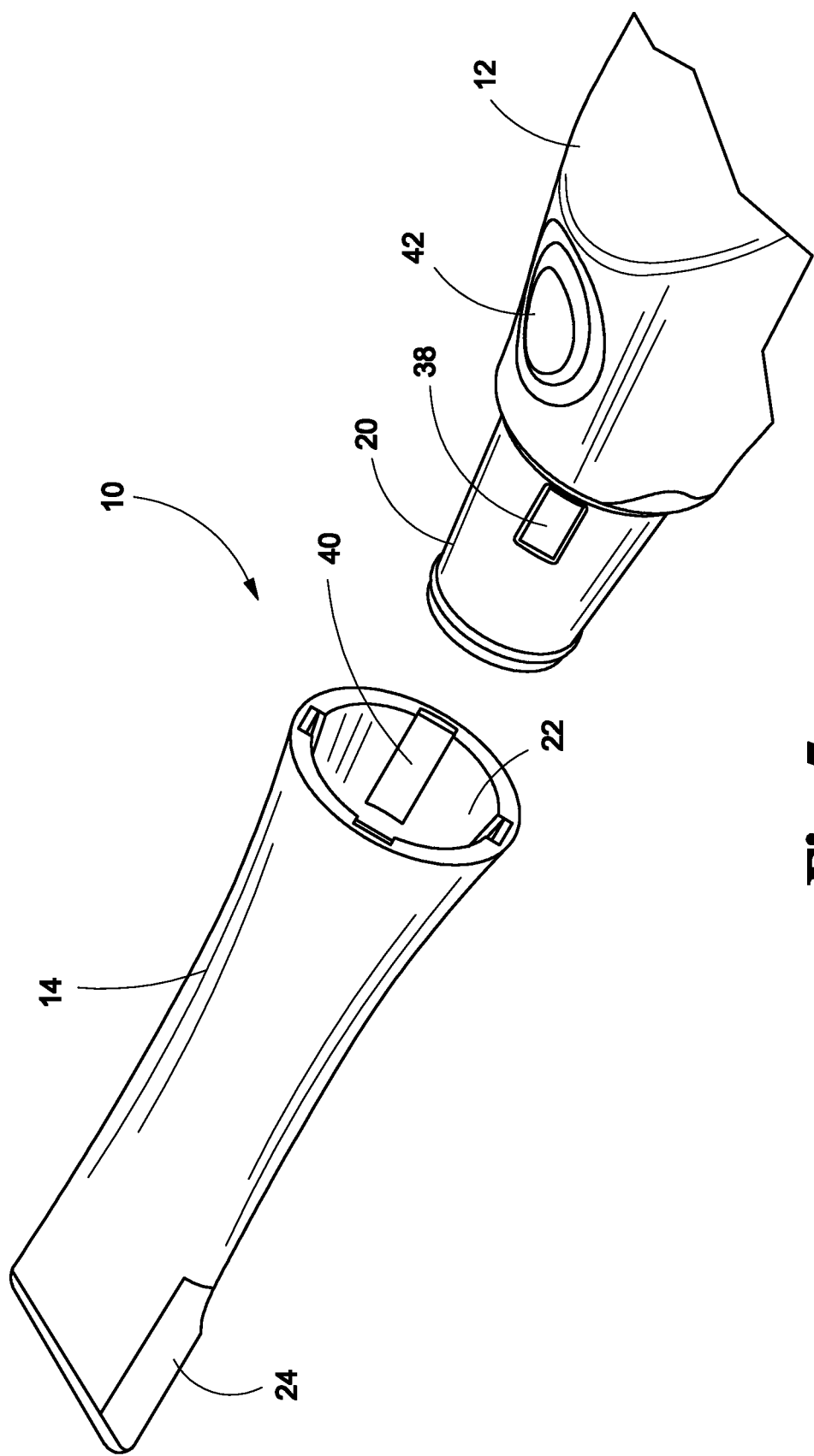

INTRAORAL SCANNER AND COMPUTING SYSTEM FOR CAPTURING IMAGES AND GENERATING THREE-DIMENSIONAL MODELS

BACKGROUND OF THE INVENTION

The present invention relates to intraoral scanning and, more particularly, to an improved intraoral scanner and computing system for capturing and producing higher quality three-dimensional imaging.

Intraoral cameras and scanners are used by dentists or doctors to take images of the inside of a patients' mouth. Current scanners commonly operate by projecting structured light such as fringes or grid patterns, collecting and analyzing imagery of the projected patterns to be measured once they are modulated by the surface of the mouth. One factor limiting performance arises from the wide diversity of the materials being scanned within the mouth. Each material has unique optical properties and thereby reflects and scatters light differently. As a result, when imaging multiple materials of the mouth simultaneously, standard imaging techniques may lead to images with low quality such as poor contrast, low luminosity or image saturation. This could lead to incomplete or inaccurate measurements.

Further, current intraoral scanners include a mouth-piece that either cannot rotate with respect to the hand-piece or cannot rotate continuously. For scanners where rotation is possible, it is typically limited to 180-degree increments. This makes operation of the scanner less convenient to the operator and less comfortable to the patient. In addition, this limitation in motion could prevent the scanner mouth-piece from accessing hard-to-reach areas in the mouth cavity, hence reducing the quality of the 3D measurements performed.

As can be seen, there is a need for an improved intraoral scanner and computing system for capturing and producing higher quality three-dimensional imaging.

SUMMARY OF THE INVENTION

In one aspect of the present invention, an intraoral scanner includes a handle, a mouthpiece extending from the handle, a structured light projector projecting a light pattern from the mouthpiece, and a stereo camera capturing images through the mouthpiece.

In some embodiments, the intraoral scanner further includes a flood illuminator projecting light from the mouthpiece.

In some embodiments, the handle includes a mounting dock and the mouthpiece includes a mounting receiver releasably coupled to the mounting dock. The mouthpiece may be rotatable relative to the handle about the mounting dock along a longitudinal axis of the intraoral scanner.

In some embodiments, the handle includes a locking pin spring biased to protrude radially from the mounting dock and a button operable to urge the locking pin inward against the bias of the spring. A plurality of pin slots may be formed circumferentially along an inner surface of the mounting receiver.

In some embodiments, the mounting receiver includes a first magnetic material and the mounting dock includes a second magnet material attracted to the first magnetic material.

In some embodiments, the light pattern is spatial modulation and/or temporal modulation. The spatial modulation may be a fringe pattern, a grid pattern, a random pattern, or a combination thereof.

In some embodiments, the capturing of images is at a video frame rate and is synchronized with the flood illuminator and the structured light projector.

In another aspect of the present invention, a system of capturing and processing image data includes an intraoral scanner having a structured light projector and a stereo camera, and a computing system operable to receive data from the intraoral scanner. The computing system includes a processor and a memory. The processor receives image data from the intraoral scanner, the image data including a plurality of images of a scene having a plurality of different materials. The processor identifies, within the plurality of images, an optimal image of each of the plurality of different materials. The processor further generates a high dynamic range image of the scene by combining the optimal images of each of the plurality of different materials. In some embodiments, the scene is an inside of a mouth of a patient.

In some embodiments, the high dynamic range image includes an overlaid pattern projected by the structured light projector and captured by the stereo camera. The processor determines three-dimensional measurements of the scene using the overlaid pattern of the high dynamic range image. The processor further generates a digital three-dimensional model of the scene using the three-dimensional measurement.

In some embodiments, the intraoral scanner further includes a flood illuminator, a handle, and a mouthpiece extending from the handle. The flood illuminator projects light from the mouthpiece, the structured light projector projects a light pattern from the mouthpiece, and the stereo camera captures images from the mouthpiece.

In another aspect of the present invention, a method of capturing and processing image data from within a patient's mouth includes the steps of: illuminating a plurality of materials within a patient's mouth with a structured light projector; capturing a plurality of images of the plurality of materials with a stereo camera; identifying, within the plurality of images, an optimal image of each of the plurality of different materials; and generating, by a computing system, a high dynamic range image of an inside of the patient's mouth by combining the optimal images of each of the plurality of different materials.

In some embodiments, the high dynamic range image includes an overlaid pattern projected by the structured light projector and captured by the stereo camera. In some embodiments, the method further includes the steps of: determining three-dimensional measurements of the inside of the patient's mouth using the overlaid pattern of the high dynamic range image; and generating, by the computing system, a digital three-dimensional model of the inside of the patient's mouth using the three-dimensional measurements.

In some embodiments, the method further includes the step of illuminating the plurality of materials within the patient's mouth with a flood illuminator. In some embodiments, the steps of illuminating a plurality of materials within the patient's mouth with the flood illuminator and the structured light projector and capturing the plurality of images of the plurality of materials with a stereo camera are performed simultaneously using an intraoral scanner.

These and other features, aspects and advantages of the present invention will become better understood with reference to the following drawings, description and claims.

BRIEF DESCRIPTION OF THE DRAWINGS

FIG. 1 is a perspective view of an embodiment of an intraoral scanner supported by a support base of the present invention;

FIG. 2 is a side view of an embodiment of an intraoral scanner supported by a support base of the present invention;

FIG. 3 is an exploded view of an embodiment of an intraoral scanner and a support base of the present invention;

FIG. 4b is a detail exploded view of an embodiment of an intraoral scanner of the present invention;

FIG. 5 is a detail exploded view of an embodiment of an intraoral scanner of the present invention;

DETAILED DESCRIPTION OF THE INVENTION

Figure 4A:
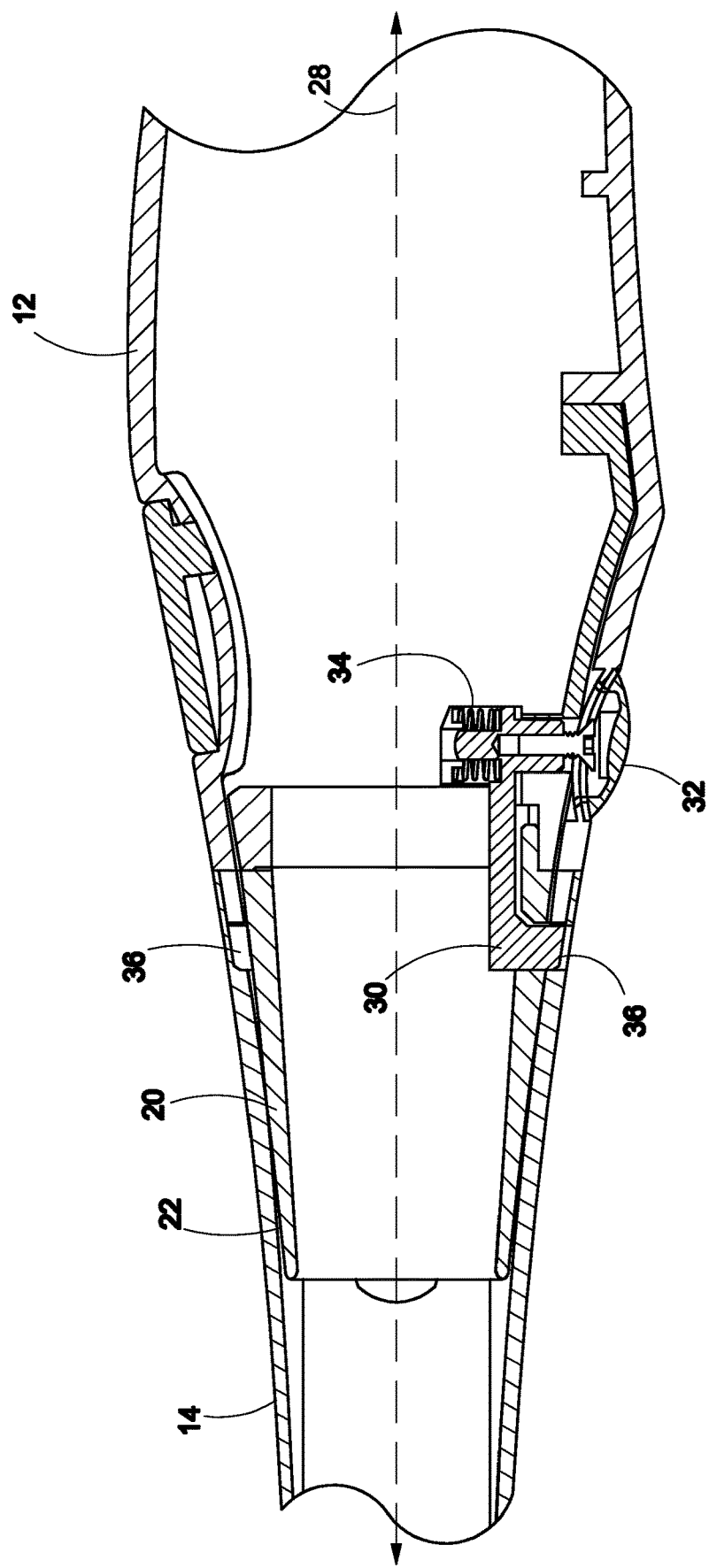
FIG. 4a is a detail cross sectional view of an embodiment of an intraoral scanner of the present invention.
Figure 6:
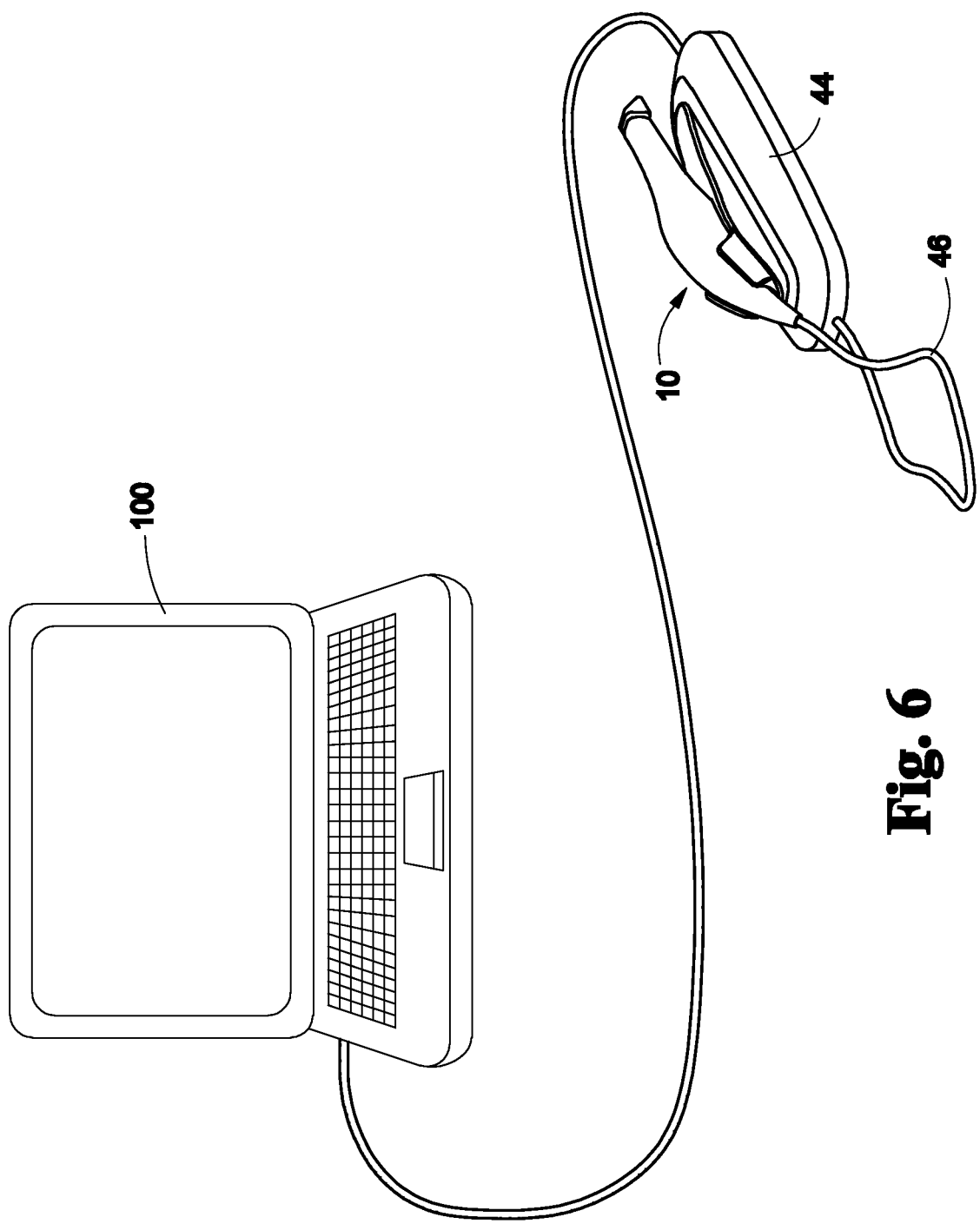
FIG. 6 is a perspective view of an embodiment of an intraoral scanner supported by a support base and connected to a computing system of the present invention.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides an intraoral scanner used in the field of digital dentistry for capturing 3D and color information of the surface of teeth, gum, dental impressions, stone models and the like. The disclosed invention also employs a hardware setup combining two 3D scanning techniques: projection of structured light and multiple-camera imaging. In addition, the introduction of a new method (voxel hashing) of encoding mutable 3D information in a scalar field yields a 3D volume with an effective resolution multiple-times greater than that achievable with traditional methods. Combined with the present inventions multimodal 3D scanning approach, the present invention creates 3D reconstruction models with enhanced accuracy.

Referring to FIGS. 1 through 8, the present invention includes an intraoral scanner 10. The intraoral scanner 10 includes a handle 12 and a mouthpiece 14 extending from the handle 12. The intraoral scanner 10 further includes a flood illuminator 16 projecting light from the mouthpiece 14 and a structured light projector 18 projecting a light pattern from the mouthpiece 14. A stereo camera 19 captures images through the mouthpiece 14.

The present invention may include a support base 44. The support base 44 is configured to releasably secure the intraoral scanner 10 when the intraoral scanner 10 is not in use. In certain embodiments, the support base 44 may supply wired or wireless power to the intraoral scanner 10. For example, the support base 44 may include a battery, which supplies power to the intraoral scanner 10. Alternatively, the support base 44 includes a power cord connected to an outlet or another power source port, such as a USB port. An electrical wiring 46 runs from the support base 44 to the intraoral scanner 10, thereby providing power to the intraoral scanner 10.

Figure 7:
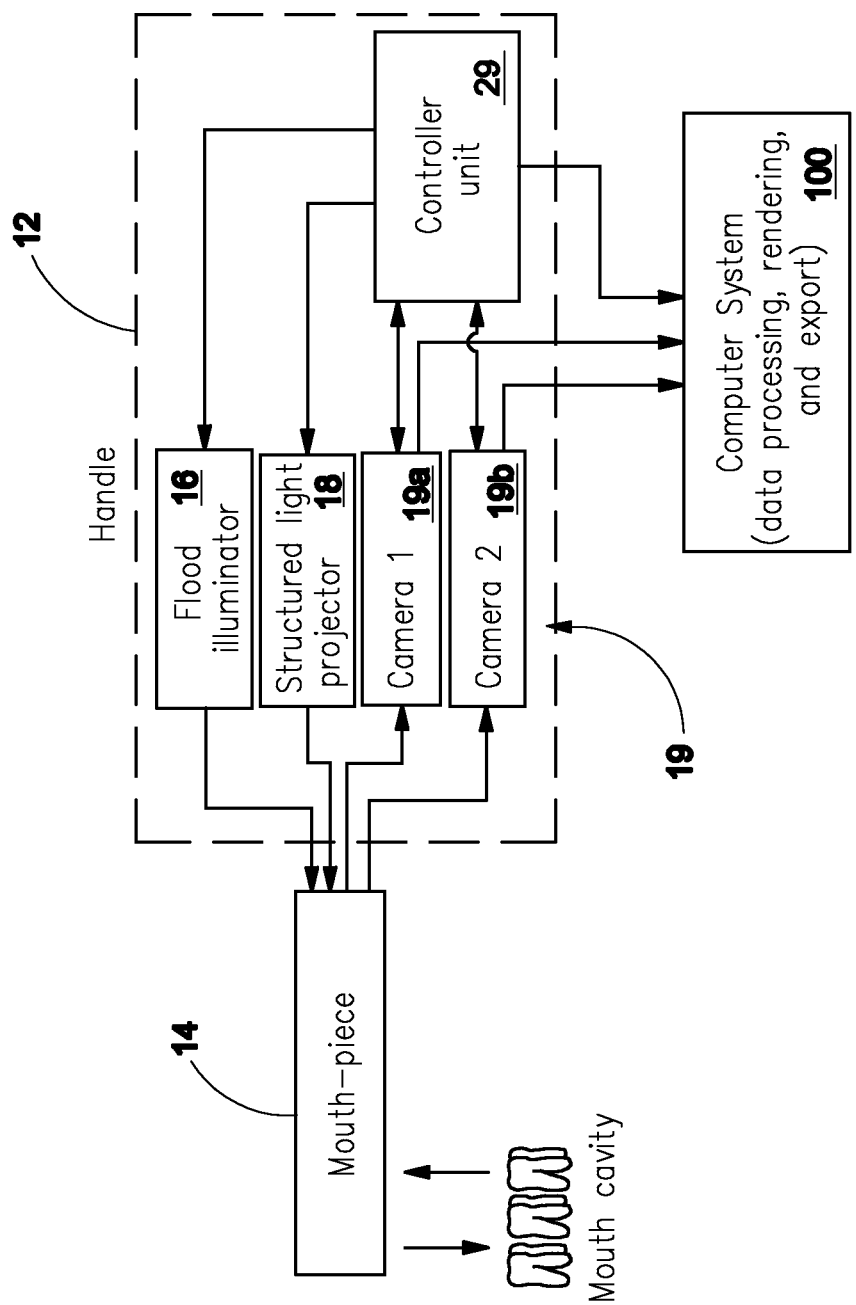
FIG. 7 is a schematic view of an embodiment of the present invention.

As illustrated in FIG. 7, the flood illuminator 16, the structured light projector 18, and the stereo camera 19 are housed within the handle 12. The intraoral scanner 10 may further include a controller unit 29 disposed within the handle. The controller unit 29 may synchronize the flood illuminator 16, the structure light projector 18, and the stereo camera 19 to activate at the same time. The controller unit 29 may further interact with and send image data to a computing system 100.

The handle 12 may further include a mounting dock 20 having an inner sidewall defining a channel 23 in which light from the flood illuminator 16 and the structured light projector 18 is projected through. In such embodiments, the mouthpiece 14 includes a mounting receiver 22 formed at a proximal end. The mounting receiver 22 releasably couples to the mounting dock 20. An outer surface of the mounting dock 20 has a shape that is defined by an inner surface of the mounting receiver 22. For example, the mounting dock 20 may include a cylindrical or frustoconical shape, while an inner surface of the mounting receiver 22 defines the cylindrical or frustoconical shape. In such embodiments, the mounting dock 20 may slide into and nest within the mounting receiver 22. An inner surface of the mouthpiece 14 also defines a channel 25 aligning with the channel 23 of the mounting dock 20. The channel 25 of the mouthpiece 14 ends at an opening 24 formed at a distal end of the mouthpiece 14.

In certain embodiments, the opening 24 may be substantially perpendicular to the channels 23, 25. In such embodiments, an angled mirror 26 is disposed at the distal end of the mouthpiece 14, within the channel 25 and above the opening 24. The angled mirror 26 may be disposed at about 30 degrees up to about 60 degrees, such as about 45 degrees, relative to the opening 24 and the channels 23, 25. Light is projected from the flood illuminator 16 and the structured light projector 18. The light travels through the aligned channels 23, 25 and is reflected off of the angled mirror 26, through the opening 24 and onto a target scene. Sensors of the stereo camera 19 capture images of the target scene from the reflection of the mirror 26.

The mouthpiece 14 may be rotatable relative to the handle 12 about a longitudinal axis 28 of the intraoral scanner. In certain embodiments, the handle 12 includes a locking pin 30 spring biased to protrude radially from the mounting dock 20 and a button 32 operable to urge the locking pin 30 inward against the bias of the spring 34. A plurality of pin slots 36 are formed circumferentially along an inner surface of the mounting receiver 22. The locking pin 30 protrudes into one of the slots 36, fixing the mouthpiece 14 to the handle 12. In certain embodiments, the pin slots 36 may be evenly spaced apart at 90-degree intervals, 45-degree intervals and the like. For example, four pin slots 36 may be evenly spaced apart 90-degrees away from one another. A user may scan a portion of the patient's mouth, remove the mouthpiece, press the button 32 to urge the locking pin 30 inward and out of a pin slot 36, rotate the mouthpiece 14 relative to the handle 12 and release the button so that the locking pin 30 enters a different pin slot 36. The user may place the mouthpiece 14 back into the patient's mouth and scan a different portion of the patient's mouth.

In certain embodiments, the handle 12 connects to the mouthpiece 14 by magnetic materials. For example, the mounting receiver 22 includes a first magnetic material 38 and the mounting dock 20 includes a second magnetic material 40 attracted to the first magnetic material 38. The first and second magnetic materials 38, 40 may include a combination of a magnet and a ferromagnet or a combination of two attracting magnets. In such embodiments, the mouthpiece 14 rotates relative to the handle 12 about a longitudinal axis 28 continuously over a full 360-degree range. This facilitates user operation when accessing hard-to-reach areas in the mouth cavity and results in the collection of more data and in turn more accurate 3D measurements.

As mentioned above, the two light sources include the flood illuminator 16 and the structured light projector 18. The two light sources may be white light sources or monochromatic sources, such as laser diodes. The light incident from both light sources is returned into the mouthpiece 14 after reflection and scattering by various objects in the mouth cavity such as teeth, gum, crowns and other dental restorations for example.

The flood illuminator 16 is an illuminator unit dedicated to illuminating the mouth cavity in a uniform manner. The light beam generated by the flood illuminator is delivered to the area of interest in the mouth cavity by the mouthpiece 14. The flood illuminator 16 allows the stereo camera 19 to capture accurate colors of the materials of the target scene.

The structured light projector 18 projects a light pattern (structured light) onto the mouth cavity, through the mouthpiece 14. The structure light projector 18 is used to project structured light onto the surface to be measured. The projected pattern can feature spatial modulation (such as fringes, grid or random patterns), temporal modulation, or a combination thereof. The projected light can be monochromatic or polychromatic.

The stereo camera 19 of the present invention includes a first camera 19a and a second camera 19b synchronously capturing images of the illuminated mouth cavity. The stereo camera 19 is a system of two cameras 19a, 19b with overlapping field-of-views, each equipped with monochromatic or color image sensors. Image capture for both sensors is synchronized in order to mitigate the effect of system motion on the resulting 3D measurements. The cameras 19a, 19b may include charge coupled device (CCD) or complementary metal-oxide semiconductor (CMOS) sensors. Each sensor captures a stream of images of the mouth cavity. In each image of the stream, various materials may be present such as teeth, gum, or filling material, for example, with an overlaid light pattern from the structured light projector 18. Synchronization of the illumination using the flood illuminator 16, illumination using the structured light projector 18 and the image capture using the stereo camera 19 is performed by the intraoral scanner 10. The capture of the stereo image pairs may occur at video frame rate and is synchronized and simultaneous with the structured light projector 18 and flood illuminator 16.

The present invention further includes a computing system 100 for processing, rendering, and exporting image data captured by the intraoral scanner 10. The computing system 100 is at least the processor and the memory. The computing system 100 may execute on any suitable operating system such as IBM's zSeries/Operating System (z/OS), MS-DOS, PC-DOS, MAC-iOS, WINDOWS, UNIX, OpenVMS, ANDROID, an operating system based on LINUX, or any other appropriate operating system, including future operating systems.

In particular embodiments, the computing system 100 includes a processor, memory, a user interface, and a communication interface. In particular embodiments, the processor includes hardware for executing instructions, such as those making up a computer program. The memory includes main memory for storing instructions such as computer program(s) for the processor to execute, or data for processor to operate on. The memory may include an HDD, a floppy disk drive, flash memory, an optical disc, a magneto-optical disc, magnetic tape, a Universal Serial Bus (USB) drive, a solid-state drive (SSD), or a combination of two or more of these. The memory may include removable or non-removable (or fixed) media, where appropriate. The memory may be internal or external to the computing system 100, where appropriate. In particular embodiments, the memory is non-volatile, solid-state memory.

The user interface includes hardware, software, or both providing one or more interfaces for user communication with the computing system 100. As an example and not by way of limitation, the user interface may include a keyboard, keypad, microphone, monitor, mouse, printer, scanner, speaker, still camera, stylus, tablet, touchscreen, trackball, video camera, another user interface or a combination of two or more of these.

The communication interface includes hardware, software, or both providing one or more interfaces for communication (e.g., packet-based communication) between the computing system 100, the intraoral scanner 10 and other computing systems or one or more networks. The intraoral scanner 10 may be directly hard wired to the computing system 100, such as through a USB port or other cable connection interface and may transfer image data through the cable connection. The intraoral scanner 10 may be hard wired to the computing system 100 through the support base 44. Alternatively, the intraoral scanner 10 may transfer image data using wireless communication. As an example, and not by way of limitation, the computing system 100 and the intraoral scanner 10 may include a communication interface including a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface. As an example and not by way of limitation, the intraoral scanner 10 and the computing system 100 may communicate via an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, the intraoral scanner 10 and the computing system 100 may communicate via a wireless PAN (WPAN) (e.g., a BLUETOOTH WPAN), a WI-FI network, a WI-MAX network, a cellular telephone network (e.g., a Global System for Mobile Communications (GSM) network), or other suitable wireless network or a combination of two or more of these. The intraoral scanner 10 and the computing system 100 may include any suitable communication interface for any of these networks, where appropriate.

As mentioned above, the computing system 100 receives image data from the intraoral scanner 10. The image data includes a plurality of images of a scene having a plurality of different materials. For example, the scene is an inside of a mouth of a patient and the plurality of different materials includes teeth, gums, crowns and other dental restorations.

The processor performs data processing such as reconstructing a 3D model, data rendering, and exporting data to a format usable by the user.

Figure 8:
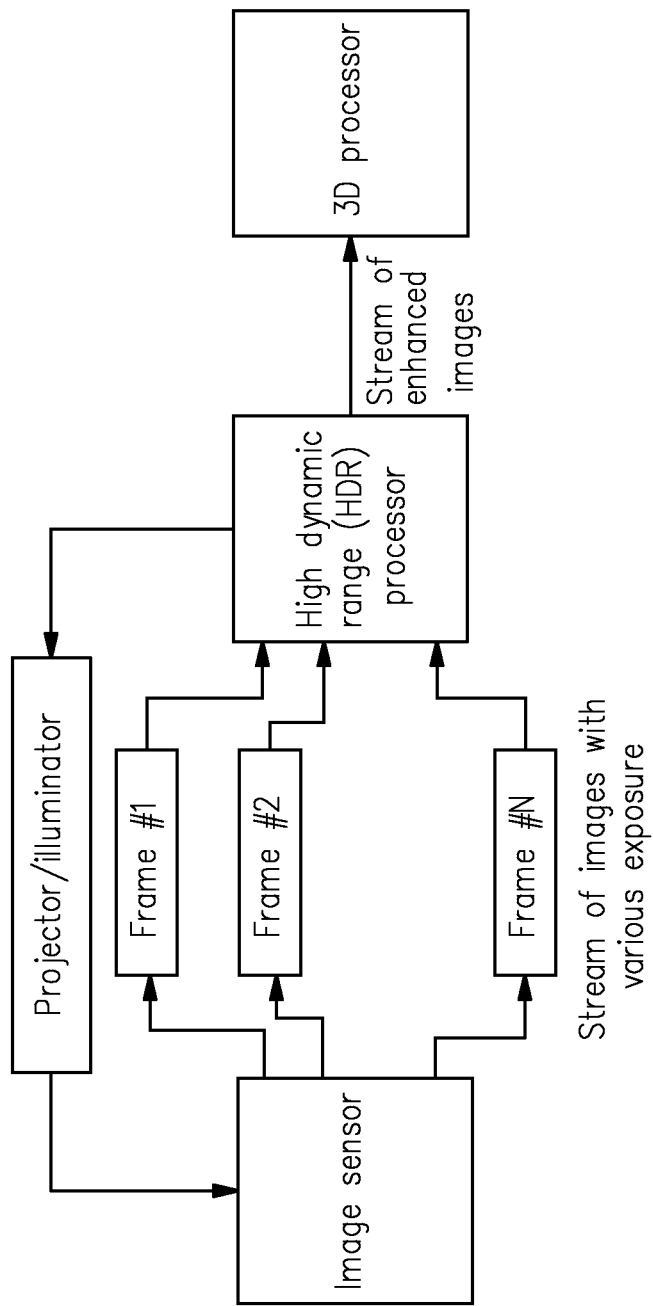
FIG. 8 is a schematic view of an embodiment of the present invention.

Referring to FIG. 8, the high dynamic range (HDR) processing stage combines images of the scene that were captured for various exposures into a single HDR image. The processor identifies, within the plurality of images, an optimal image of each of the plurality of different materials and generates the HDR image of the scene by combining the optimal images of each of the plurality of different materials. The computer system 100 selects the optimal image based on the exposure for each of the materials visible in the frame. The exposure of the image can be controlled in two ways: by modifying the exposure time of the image capture or by modifying the intensity (luminance) of the illuminator or projector used. The exposure of the frame is selected so that image areas for one material exhibit good image quality (i.e. clear contrast and high luminosity). This means that areas with other materials visible in the frame could have lower quality (for example they could become over-exposed or under-exposed). Images of the same scene with various exposures are collected sequentially. This allows collecting high quality images for each material (area).

The HDR image exhibits image quality that is higher than any of the original images captured due to varying exposures. The present invention allows for better visualization of details in the images, and especially when imaging various materials such as tooth, gum, filling, or stone/gypsum. The method also reduces image saturation (glint effect) encountered in the presence of wetness (saliva or blood) on the surface of the tooth or gum which is detrimental to the performance of intraoral systems. The HDR processing stage can be implemented as a digital image processor using a software approach (computer code) or a hardware approach [such as Field-Programmable Gate Arrays (FPGA's) or multi-processor units] or a combination of both.

The HDR-enhanced image is then used for computation of the 3D measurements. The detection and identification of the projected pattern is facilitated by using the HDR-enhanced imagery. The HDR image includes the overlaid pattern projected by the structured light projector and captured by the stereo camera. The computing system 100 determines three-dimensional measurements of the scene using the overlaid pattern of the high dynamic range image and generates a digital three-dimensional model of the scene using the three-dimensional measurements. Using the combination of the stereo cameras 19 and the structured light projector 18, the measurements are more accurate and complete. Another benefit of this method is that the remainder of the 3D measurement pipeline does not need to be altered for processing HDR-enhanced data instead of regular data.

A method of capturing and processing image data from within a patient's mouth includes the following steps. An operator inserts the mouthpiece 14 into a patient's mouth. The operator presses a button 42 to turn on the flood illuminator 16 and the structured light projector 18, thereby illuminating a plurality of materials within the patient's mouth. The button 42 simultaneously activates the stereo camera 19 which captures images of the plurality of materials inside of the patient's mouth. The digital images are saved on a memory. The operator may then remove the mouthpiece 14 from the patient's mouth and rotate the mouthpiece relative to the handle 12. The operator then inserts the mouthpiece 14 back into the patient's mouth and presses the button 42 to capture and save additional digital images. The above steps may be repeated until the operator has captured a sufficient amount of digital images to reconstruct a target scene.

The method further includes processing the above captured digital images. The image data is sent to the computing system 100 for processing, rendering, and exporting. An optimal image of each of the plurality of different materials is identified by the computing system 100. A high dynamic range image of the target scene is generated by combining the optimal images of each of the plurality of different materials by the computing system 100. The optimal images are selected based on the materials exposure quality. The computing system 100 selects the exposure for each image based on the materials visible in the frame.

The method further includes rendering a three-dimensional image of the scene. As mentioned above, the high dynamic range image includes the overlaid pattern projected by the structured light projector 18 and captured by the stereo camera 19. The computer system 100 determines three-dimensional measurements of the inside of the patient's mouth using the overlaid pattern of the high dynamic range image. The computer system 100 generates a digital three-dimensional model of the inside of the patient's mouth using the three-dimensional measurements.

Figures 9, 10:
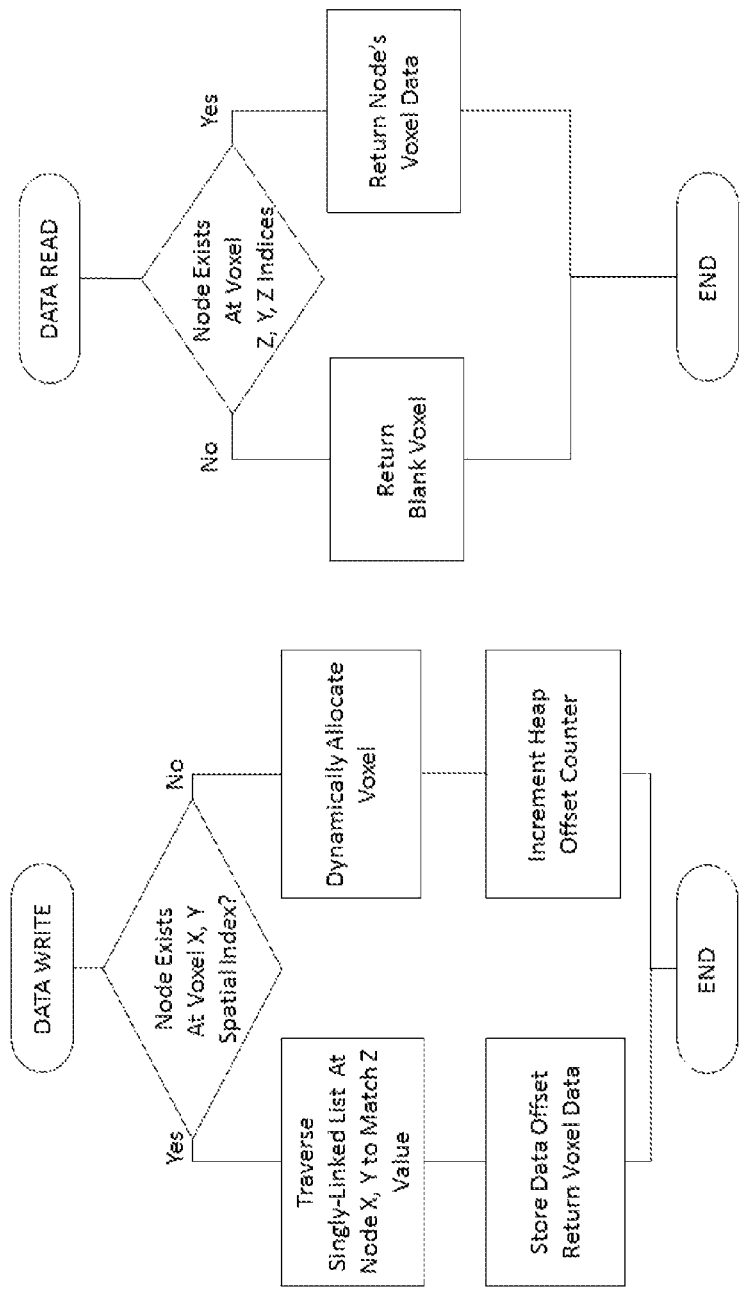
FIG. 9 is a flow chart of an embodiment of voxel hashing of the present invention.
FIG. 10 is a flow chart of an embodiment of voxel hashing of the present invention.

Referring to FIGS. 9 and 10, other aspects of the present invention include an improved system and method for 3D data processing, to include 3D data collection, storage and processing. With these improvements greater 3D resolution can be achieved, and faster 3D measurements can be made. In addition, the amount of memory required to represent the 3D scalar volume data is substantially reduced.

Within the field of 3D scanning, 3D information is traditionally encoded in a scalar volume described by a truncated signed distance function (TSDF). The dimensions of this scalar volume are fixed and determined by the available memory of the device on which the information is stored, by way of non-limiting example, the device may include a graphics processing unit (GPU), a central processing unit (CPU), or a field-programmable gate array (FPGA).

Traditionally, the memory block representing the scalar volume must be allocated at run-time and is static. Thus, the required memory increases with an inverse-cubic relationship to the voxel size. For example, doubling the resolution of the scalar volume (or halving the voxel size) requires eight-times more device memory, while tripling the resolution requires a 27-times more memory, and so on.

To overcome this limitation and to maximize resolution (and thus minimize voxel size) of the scalar volume, a novel approach of dynamic voxel allocation may be employed. In contrast to statically allocating the entire volume at runtime, voxels are instead allocated as needed when their weights/values are modified beyond a non-zero default.

Traditional scalar volumes directly map voxels to their respective memory addresses in a contiguous memory block by using the X, Y, and Z index in the following approach, where subscript index is the per-axis spatial index of the voxel in the volume, and subscript dim is the dimension in voxels of the volume along the respective axis:

$$\text{Memory Address} = X_{index} + (Y_{index} * X_{dim}) + (Z_{index} * Y_{dim} * X_{dim})$$

In contrast, the method of the present invention uses a hash key to represent the spatial index of the voxel. This hash key is then stored in a two-dimensional hash table to correlate each allocated voxel's respective hash key to a memory block in a pre-allocated heap.

The hash key itself stores at the very least the X, Y, and Z spatial indices of the voxel it represents. Additional information can also be encoded in the key, such as a culling/removal bit.

By way of non-limiting example, for a 40-bit voxel hash key, the hash key may include three 13-bit keys describing each of the X, Y, and Z spatial indices of the voxel within the scalar volume and one 1-bit culling flag (indicating that the voxel is no longer used and should be removed). The 40-bit voxel hash key provides for a scalar volume with a maximum dimensionality of $2^{13} \times 2^{13} \times 2^{13}$ voxels, or 8192×8192× 8192 voxels.

In order to retrieve or allocate voxel data in memory, a combination of a two-dimensional hash table and a pre-allocated voxel heap are used. In addition, a mutable offset value (heap pointer) is used to keep track of the next block in the pre-allocated heap available for dynamic allocation. Continuing with the 40-bit voxel hash key example, the hash table instantiated with $2^{13} \times 2^{13}$ bucket nodes in size, representing each of a voxel's possible X, Y spatial indices within the scalar volume.

Each of these bucket nodes represent the head of a singly-linked list of child nodes, with each child node containing data describing the next node in the singly-linked list (if there is a next node) and an offset in the pre-allocated voxel heap representing the node's respective voxel's data block.

When a voxel is addressed in the hashed scalar volume, one of two operations will be made: reading or writing of the voxel's data.

If writing of the voxel data is required, the X, Y, and Z spatial indices of the requested voxel is passed to a lookup-function. This lookup-function first checks the hash table to determine if the bucket node at the requested voxel's X, Y spatial index contains a data offset representing any voxel's data block.

If, indeed, the bucket node contains a valid data offset, the lookup-function will traverse the list until the "next node" value of the child node(s) yields a null value, thus indicating the end of the singly-linked list. During this traversal, the child nodes' respective voxel data is checked for its hash key, from which its respective spatial Z index is extracted. If this spatial Z index matches the requested spatial Z index, then the data offset stored in that node (and thus the voxel data itself) is returned.

However, if the requested voxel is not found (or if the bucket node itself contains no data offset), the lookup-function then dynamically allocates a single voxel. This is done by first atomically incrementing the heap pointer while simultaneously taking old value prior to the increment. This offset value represents this newly allocated voxel's block of memory. This offset value is then stored in the next available child node (or bucket node if no child node exists at the X, Y spatial index), and the node is inserted into the list at the voxel's respective X, Y spatial index.

If reading of the voxel data is required, the same process occurs, but no dynamic allocation occurs if the requested voxel (at its spatial X, Y, and Z indices) is not found in the hash table. Instead in this case, a "blank" or zero-valued voxel is returned, denoting a vacant voxel at the requested spatial index.

Because a vast majority of the voxels in a traditional TSDF volume are never occupied, accessed, nor needed, a great deal of otherwise usable memory is wasted if the vacant voxels are allocated. The hashing approach of the present invention instead allows for only occupied voxels to be represented in memory. By limiting memory allocation to descriptive voxels, the effective resolution of the 3D volume may be greatly increased and the effective size of the voxel may be greatly reduced. In turn, this results in a much more accurate 3D reconstruction.

The use of algorithms based on the truncated signed distance function (TSDF) combined with a scalar volume encoded by voxel hashing yields a much finer and detailed 3D representation of three-dimensional scenes and scans. In the context of the enhanced intraoral three-dimensional measurement according to other aspects of the invention, this results in faster measurements of a patient's oral cavity having an enhanced 3D resolution.

It should be understood, of course, that the foregoing relates to exemplary embodiments of the invention and that modifications may be made without departing from the spirit and scope of the invention as set forth in the following claims.

What is claimed is:

1. An intraoral scanner comprising:
   a handle having a mounting dock;
   a mouthpiece extending from the handle, the mouthpiece having a mounting receiver releasably coupled to the mounting dock;
   a structured light projector projecting a light pattern from the mouthpiece; and
   a stereo camera capturing images through the mouthpiece, wherein the handle further comprises a locking pin spring biased to protrude radially from the mounting dock and a button operable to urge the locking pin inward against the bias of the spring, wherein a plurality of pin slots are formed circumferentially along an inner surface of the mounting receiver.

2. The intraoral scanner of claim 1, further comprising a flood illuminator projecting light from the mouthpiece.

3. The intraoral scanner of claim 2, wherein the mouthpiece is rotatable relative to the handle about the mounting dock along a longitudinal axis of the intraoral scanner.

4. The intraoral scanner of claim 2, wherein the capturing of images is at a video frame rate and is synchronized with the flood illuminator and the structured light projector.

5. The intraoral scanner of claim 1, wherein the mounting receiver comprises a first magnetic material and the mounting dock comprises a second magnet material attracted to the first magnetic material.

6. The intraoral scanner of claim 1, wherein the light pattern is at least one of spatial modulation and temporal modulation.

7. The intraoral scanner of claim 1, wherein the spatial modulation is at least one of a fringe pattern, a grid pattern, and a random pattern.

8. A system of capturing and processing image data comprising:
   an intraoral scanner comprising a structured light projector and a stereo camera;
   a computing system operable to receive data from the intraoral scanner, the computing system comprising a processor and a memory, wherein the processor
   receives image data from the intraoral scanner, wherein the image data comprises a plurality of images of a scene having a plurality of different materials;
   identifies, within the plurality of images, an optimal image of each of the plurality of different materials; and
   generates a high dynamic range image of the scene by combining the optimal images of each of the plurality of different materials, wherein the high dynamic range image comprises an overlaid pattern projected by the structured light projector and captured by the stereo camera.

9. The system of claim 8, wherein the processor:
determines three-dimensional measurements of the scene using the overlaid pattern of the high dynamic range image; and
generates a digital three-dimensional model of the scene using the three-dimensional measurement.

10. The system of claim 8, wherein the scene is an inside of a mouth of a patient.

11. The system of claim 8, wherein the intraoral scanner further comprises a flood illuminator, a handle, and a mouthpiece extending from the handle, wherein the flood illuminator projects light from the mouthpiece, the structured light projector projects a light pattern from the mouthpiece, and the stereo camera captures images from the mouthpiece.

12. An intraoral scanner comprising:
a handle;
a mouthpiece extending from the handle;
a structured light projector projecting a light pattern from the mouthpiece;
a flood illuminator projecting light from the mouthpiece; and
a stereo camera capturing images through the mouthpiece, wherein the capturing of images a at a video frame rate and a synchronized with the flood illuminator and the structured light projector.

13. The intraoral scanner of claim 12, wherein the mouthpiece is rotatable relative to the handle along a longitudinal axis of the intraoral scanner.

14. The intraoral scanner of claim 12, wherein the mounting receiver comprises a first magnetic material and the mounting dock comprises a second magnet material attracted to the first magnetic material.

15. The intraoral scanner of claim 12, wherein the light pattern is at least one of spatial modulation and temporal modulation.

16. The intraoral scanner of claim 15, wherein the spatial modulation is at least one of a fringe pattern, a grid pattern, and a random pattern.

* * * * *